Figure 1:
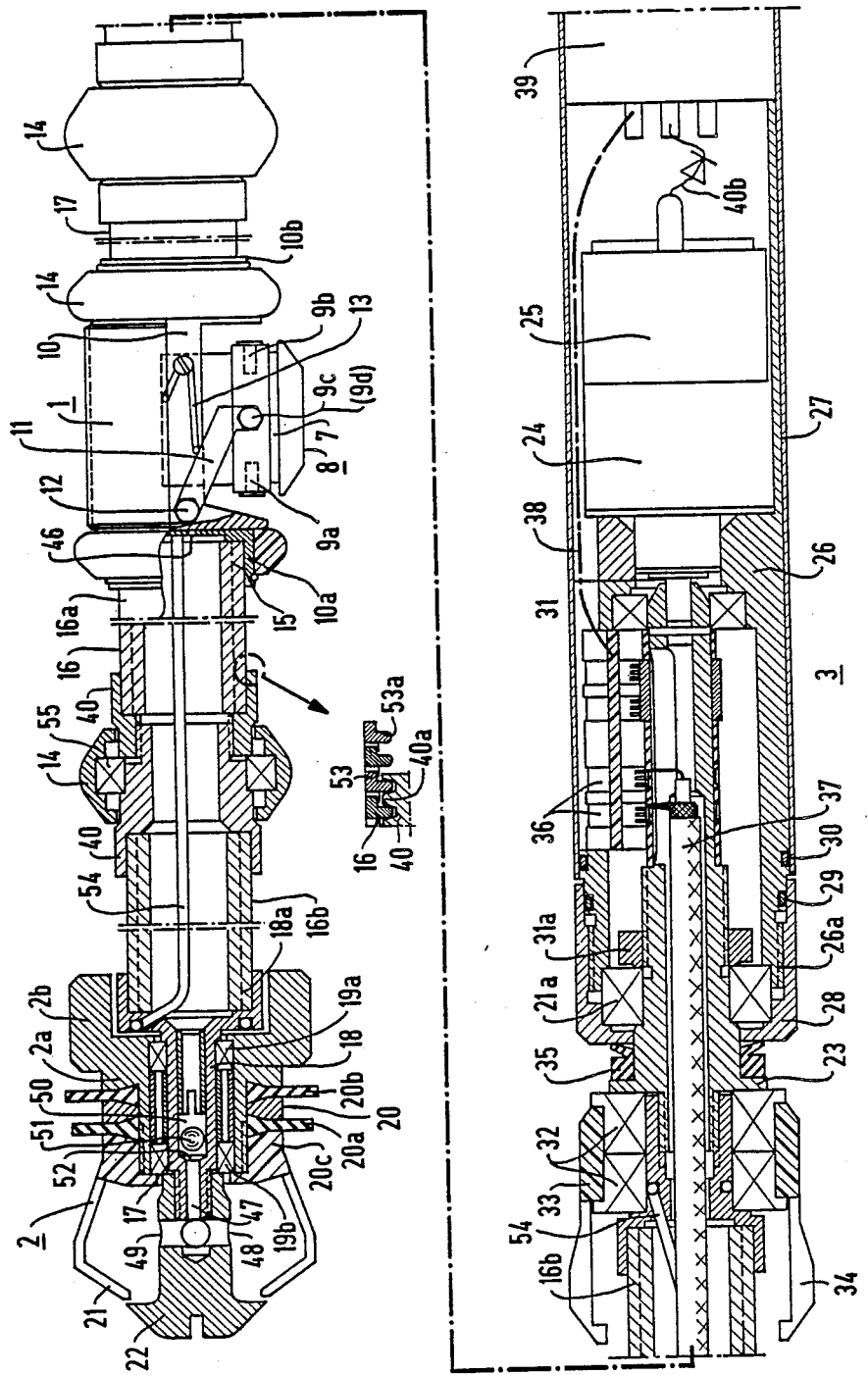

United States Patent [19]

Adams et al.

[11] Patent Number: 4,981,044
[45] Date of Patent: Jan. 1, 1991

[54] ULTRASONIC SENSOR FOR TESTING U-SHAPED TUBES OF A HEAT EXCHANGER

[75] Inventors: Helmar Adams, Erlangen; Peter Hertel, Neunkirchen Am Brand; Heinz Jacob, Memmelsdorf, all of Fed. Rep. of Germany

[73] Assignee: Siemens Aktiengesellschaft, Munich, Fed. Rep. of Germany

[21] Appl. No.: 365,973

[22] Filed: Jun. 14, 1989

[30] Foreign Application Priority Data

Jun. 15, 1988 [DE] Fed. Rep. of Germany ....... 3820422

[51] Int. Cl.$^5$ ............................................. G01N 29/04
[52] U.S. Cl. ........................................................ 73/623
[58] Field of Search .................... 73/622, 623, DIG. 9, 73/638, 644; 376/249

[56] References Cited

U.S. PATENT DOCUMENTS

| 4,241,609 | 12/1980 | Bergman et al. | 73/623 |
| 4,523,470 | 6/1985 | Müller et al. | 73/623 |
| 4,586,380 | 5/1986 | Patterson | 73/623 |
| 4,612,808 | 9/1986 | McKirdy et al. | 73/622 |
| 4,872,347 | 10/1987 | Okabe et al. | 73/622 |

FOREIGN PATENT DOCUMENTS

| 0086341 | 8/1983 | European Pat. Off. |  |
| 0276819 | 8/1988 | European Pat. Off. |  |
| 0108488 | 9/1978 | Japan | 73/623 |
| 0109490 | 8/1979 | Japan | 73/623 |

Primary Examiner—John Chapman
Assistant Examiner—Louis M. Arana
Attorney, Agent, or Firm—Herbert L. Lerner; Laurence A. Greenberg

[57] ABSTRACT

An ultrasonic sensor for testing tubes of a heat exchanger having a U-shaped tube bundle includes a probe head unit having an ultrasonic vibrator and two opposite ends. Two flexible hollow shafts are each connected to a respective one of the ends of the probe head unit. One of the hollow shafts is rotatably supported in a guide tip and the other of the hollow shafts is rotatably supported in a cylindrical sheath. An electric drive unit is connected to and fixed against torque relative to the other hollow shaft. The flexible hollow shafts have supports at predetermined axial intervals. A sealing body is connected to the cylindrical sheath for sealing off a flow of a fluid for coupling the ultrasonic vibrator and a pusher hose is also connected to the cylindrical sheath.

5 Claims, 2 Drawing Sheets

ULTRASONIC SENSOR FOR TESTING U-SHAPED TUBES OF A HEAT EXCHANGER

The invention relates to an ultrasonic sensor for testing tubes of a heat exchanger having a U-shaped tube bundle or nest, such as are used, for example, in steam generators in nuclear power plants.

Published European application No. 0 086 341 discloses an ultrasonic sensor for non-destructive testing of cylindrical hollow spaces, which is provided with a rotating probe head that is rotatably supported at one end in a guide and at the other in a cylindrical, rigid sheath. The probe head includes a holder body containing an ultrasonic vibrator disposed in a radially extending bore, that is, transversely to the longitudinal axis of the sensor. That ultrasonic vibrator is disposed in the bore in such a way that it is displaceable in the radial direction and is firmly clamped with a screw. A coupling fluid is supplied to the ultrasonic vibrator through a hose guided by the sensor. An electric motor with a step-down gear that is accommodated inside the rigid cylindrical sheath of the sensor is used to drive the rotating probe head. Adjoining the sheath is a guide portion having a sealing body, to which a pusher hose is secured. A pusher apparatus with which the sensor is thrust into the tube of the heat exchanger to be tested, is associated with the pusher hose.

Such a prior art ultrasonic sensor can only be used for testing straight portions of the tubes of the tube bundle of a heat exchanger. It is not possible to feed the ultrasonic sensor into the curved portion of the tubes of a tube bundle.

It is accordingly an object of the invention to provide an ultrasonic sensor for testing U-shaped tubes of a heat exchanger, which overcomes the hereinafore-mentioned disadvantages of the heretofore-known devices of this general type, which is simply constructed and with which the ultrasound measurements can be made even in the curved region of a U-shaped tube.

With the foregoing and other objects in view there is provided, in accordance with the invention, an ultrasonic sensor for testing tubes of a heat exchanger having a U-shaped tube bundle, comprising a probe head unit having an ultrasonic vibrator and two opposite ends, two flexible hollow shafts each being connected to a respective one of the ends of the probe head unit, a guide tip in which one of the hollow shafts is rotatably supported, a cylindrical sheath in which the other of the hollow shafts is rotatably supported, an electric drive unit connected to and fixed against torque relative to the other hollow shaft, the flexible hollow shafts having supports at predetermined axial intervals, a sealing body connected to the cylindrical sheath for sealing off a flow of a fluid for coupling the ultrasonic vibrator, and a pusher hose connected to the cylindrical sheath.

In this way, the drive forces that must be brought to bear for the rotational motion of the probe head in the vicinity of the curve of the tube can be kept low, so an electric motor accommodated in the sensor can be used to drive the probe head, despite the small size of the motor.

The coupling fluid emerges from the sealing body in the downstream direction, as seen in the insertion direction of the sensor, and fills the space between the inner wall surface of the tube to be tested and the surface of the sensor, so that good sliding of the supports is also assured.

In accordance with another feature of the invention, there is provided another sealing body disposed on the outer periphery of the guide tip, in addition to the sealing body disposed on the cylindrical sheath. This is done in order to prevent the coupling fluid from escaping during the transition of the guide tip from the upwardly oriented position to the downwardly oriented position in the tube curve.

In accordance with a further feature of the invention, the guide tip has at least one outlet opening formed therein for the coupling fluid used for coupling the ultrasonic vibrator. This provides a further improvement in the sliding characteristics of the sensor and therefore a reduction in the drive forces. With this feature, the guide tip and the supports preceding the probe head are moistened upon insertion of the sensor into the tube to be tested, so that these parts slide more easily.

In accordance with an added feature of the invention, the supports are slide rings.

In accordance with an additional feature of the invention, the supports are rings, and there are provided ball bearings supporting the rings on the flexible hollow shafts. This reduces the friction of the sensor on the inner wall surface of the tube to a minimum, so that the drive force for the motor unit can be kept particularly low.

In accordance with yet another feature of the invention, there is provided a shutoff valve upstream of the outlet opening, the shutoff valve including means for permitting fluid flow through the outlet or for uncovering the outlet to a tube to be tested when the guide tip assumes or enters an upwardly oriented position and for blocking fluid flow through the outlet when the guide tip assumes or enters a downwardly oriented position, by utilizing gravity. As a result, in the transition of the guide tip from the upwardly oriented to the downwardly inclined position, the ultrasonic vibrator coupling fluid is prevented from escaping from the tube to be tested.

In accordance with yet a further feature of the invention, there is provided a holder or retaining body from which the ultrasonic vibrator is cardanically suspended. This provides good adaptation of the probe head to the curvature of the inner tube wall surface in the curved region.

In accordance with a concomitant feature of the invention, the flexible hollow shafts are formed of helically wound spring wire having mutually interlocking windings.

Other features which are considered as characteristic for the invention are set forth in the appended claims.

Although the invention is illustrated and described herein as embodied in an ultrasonic sensor for testing U-shaped tubes of a heat exchanger, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 2:
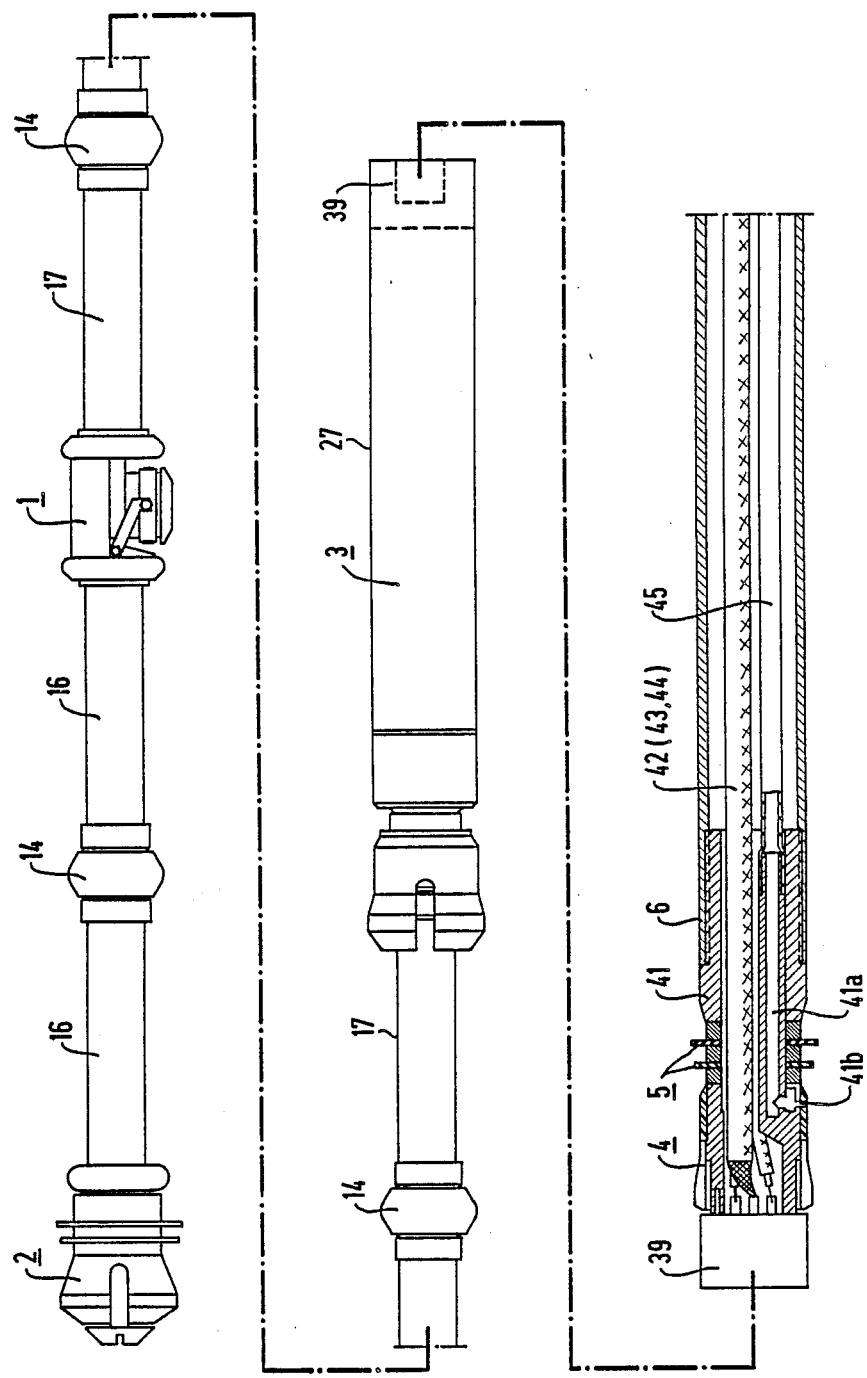

FIG. 1 is an exploded fragmentary, diagrammatic, longitudinal-sectional view showing details of the forward portion of an ultrasonic sensor on an enlarged scale; and FIG. 2 is an exploded partly elevational and partly sectional view of the entire sensor with details of the rear portion.

Referring now to the figures of the drawing in detail and first, particularly, to FIG. 2 thereof, there is seen an ultrasonic sensor having a probe head unit 1 that is rotationally supported at opposite ends thereof through respective hollow shafts 16 and 17. The hollow shaft 16 is in turn supported in a guide tip 2 and the hollow shaft 17 is in turn supported in a drive and signal transmission unit 3. Supports 14 are disposed at predetermined axial intervals along the flexible hollow shafts 16, 17.

The drive and signal transmission unit 3 is adjoined by a guide segment 4 having a sealing body 5 with discs, to which a pusher hose 6 is secured. The sensor is thrust into the tube of a heat exchanger through the use of the pusher hose 6. A pusher apparatus, which is known in the art, is used for this purpose.

As FIG. 1 shows in a longitudinal section, the probe head unit 1 has a holder 10 for a probe head 8 with an ultrasonic vibrator 7. The probe head is movable through bearing journals 9a, 9b, 9c, 9d in two axes which are at right angles to one another. In other words, the probe head is cardanically suspended. The bearing journals 9a-9d are suspended on the holder 10 through two parallel rocking levers 11 and joints 12. A spring 13 secured to the holder 10 acts through the rocking lever 11 to press the probe head 8 against the inner wall surface of the tube to be tested.

Both ends of the holder 10 are provided with extensions 10a, 10b on which the supports 14, which are constructed in the form of slide rings, are secured. The extension 10a has a female thread 15, into which one end 16a of the flexible hollow shaft 16 is screwed. The hollow shaft 16 is provided with one or more of the supports 14. The other end 16b of the flexible hollow shaft 16 is screwed into a female thread 18a of a shaft journal 18, which is rotatably disposed in a jacket 2a of the guide tip 2 through two ball bearings 19a, 19b. The jacket 2a has a collar 2b serving as a support in the tube, and another sealing body 20 which is constructed in the form of two rubber washers 20a, 20b, which are retained by a screw cap 20c. Elastic guide tongues 21 which are bent toward an end piece 22 of the guide tip 2, are disposed on the screw cap 20c. The end piece 22 is frustoconical and is screwed onto the shaft journal 18.

On the drive side, the holder 10 the extension 10b of the probe head 8 also has a female thread 15 into which an elastic hollow shaft 17 is screwed. The hollow shaft 17 is connected through a plurality of non-illustrated interposed supports 14 and a hollow shaft journal 23 to the drive and signal transmission unit unit 3, which includes a step-down gear 24 and an electric motor 25, in such a manner as to be fixed against relative torque. The drive and signal transmission unit 3 is disposed on a shell body 26, on which the shaft journal 23 is also supported, through a ball bearing 31. The shell body 26 is surrounded by a sheath 27 and is detachably connected thereto. In the direction toward the probe head, the end of the shell body 26 has a hood 28, which is screwed onto a thread 26a of the shell body 26. Respective ring seals 30, 29 are disposed between the sheath 27 and shell body 26 and between the hood 28 and shell body 26 for sealing purposes. A ball bearing 21a is anchored on the shaft journal 23 with an eye nut 31a.

Besides the hood 28, a double roller bearing 32 is also disposed on the shaft journal 23. The double roller bearing 32 has an outer bearing body 33 which is provided with finger-like elastic laminations 34 for supporting the drive unit 3 on the tube to be tested. A V-ring seal 35 is also disposed between the hood 28 and the double roller bearing 32, for sealing off the interior of the drive unit from the ingress of coupling fluid. Various slide contacts 36 are disposed in the interior of the drive unit, between the eye nut 31a and the ball bearing 31. These contact 36 transmit electrical ultrasonic vibrator signals transmitted through a cable 37 to stationary connection lines 38 leading to a plug 39 on the end of the shell body 26. Additional lines 40b, with an interposed diode, lead from the electric motor 25 to the plug 39. The plug 39 includes a bayonet mount, for the sake of easy mechanical and electrical disconnection of the drive unit 3 from the guide segment 4 shown in FIG. 2.

A coaxial cable 42 for transmitting the electrical signals of the ultrasonic vibrator is provided in the pusher hose 6 which is connected to the guide segment 4 by means of a coupler 41 and the sealing body 5. A further cable 43 serves to supply voltage to the motor, which is operated with direct current. Another cable 44 transmits signals from which the rpm and angular position of the probe head are derived.

Also accommodated in the thrust hose 6 is a hose 45, which extends as far as the guide segment 4 and serves to deliver fluid, such as water, used to couple the vibrator. A conduit 41a, which is provided in the coupler and into which the hose is threaded, is provided with outlet openings 41b, so that the coupling fluid can flow to the ultrasonic vibrator 7 and as far as the rubber washers 20a, 20b of the guide tip 2, through the space defined by the inner wall surface of the tube to be tested, the disks of the sealing body 5, and the sheath 27.

As FIG. 1 shows, the rotatable part of the hollow shaft 16a or the shaft journal 18 or the holder 10 has an opening 46, leading from the outside in, through which the coupling fluid can reach the hollow space of the shaft journal 18. A bore 47 leads from the hollow space of the shaft journal 18 to the end piece 22 of the guide tip 2, which is provided with outlet openings 48, 49 leading toward the angularly bent laminations 21.

A shutoff valve 50 is disposed in the hollow space of the shaft journal 18 upstream of the outlet openings and is constructed in such a way that by utilizing gravity, the valve outlet leading to the tube to be tested is uncovered as long as the guide tip 2 of the ultrasonic sensor is in an upwardly oriented position, and the valve outlet is closed whenever the guide tip 2 enters a downwardly oriented position. As a result, as the sensor is introduced into the upwardly oriented curved portion of the tube to be tested, the laminations 21 on the guide tip 2, which are used for guidance and are bent at an angle and the sealing rings 20a, 20b are moistened with fluid, so that the sensor slides more easily. At the transition of the guide tip 2 from the upwardly oriented location in the tube to the downwardly inclined location, the shutoff valve 50 closes, so that the coupling fluid cannot run out of the guide tip 2. The shutoff valve 50 may simply be constructed as a ball valve with a sealing seat 52, in which case whenever the guide tip 2 enters a downward inclined position, a ball 51 rests on the sealing seat 52 due to gravity and prevents a flow of the fluid through it. In the other position of the guide tip, the ball 51 assumes a position in which the flow of fluid is allowed.

It is advantageous to form the hollow shafts 16 and 17 from hollow shaft lengths, and to join them together, with the supports 14 inbetween.

As shown in the enlarged portion of FIG. 1 below one of the supports 14, the flexible hollows shafts 16, 17 are preferably formed of a helically wound spring wire 53, the windings of which interlock with one another. The windings have helical ribs 53a that form a male thread. The supports 14 have annular extensions 40 on both ends, which are provided with a female thread 40a, so that the hollow shafts or shaft segments 16, 17 can be screwed into the supports and secured. The supports 14 are suitably constructed in the form of rings, which are supported through ball bearings 55 on the flexible hollow shafts or shaft segments 16, 17. A rope or cable 54 is guided through the sensor, anchored to the guide tip 2, and used to pull the entire sensor out of the tube to be tested. At the site where the ultrasonic vibrator 7 is installed, the rope 54 is wrapped around the cardanically suspended head.

We claim:

1. Ultrasonic sensor for testing tubes of a heat exchanger having a U-shaped tube bundle, comprising a probe head unit having an ultrasonic vibrator and two opposite ends, two flexible hollow shafts each being connected to a respective one of said ends of said probe head unit, a guide tip in which one of said hollow shafts is rotatably supported, a cylindrical sheath in which the other of said hollow shafts is rotatably supported, an electric drive unit connected to and fixed against torque relative to said other hollow shaft, said flexible hollow shafts having supports at predetermined axial intervals, a sealing body connected to said cylindrical sheath for sealing off a flow of a fluid for coupling said ultrasonic vibrator, a pusher hose connected to said cylindrical sheath, another sealing body disposed on the outer periphery of said guide tip, said guide tip having at least one outlet opening for coupling fluid formed therein, and a shutoff valve upstream of said outlet opening, said shutoff valve including means for permitting fluid flow through said outlet to a tube to be tested when said guide tip assumes an upwardly oriented position and for blocking fluid flow through said outlet when said guide tip assumes a downwardly oriented position, by utilizing gravity.

2. Ultrasonic sensor according to claim 1, wherein said supports are slide rings.

3. Ultrasonic sensor according to claim 1, wherein said supports are rings, and including ball bearings supporting said rings on said flexible hollow shafts.

4. Ultrasonic sensor according to claim 1, including a holder from which said ultrasonic vibrator is cardanically suspended.

5. Ultrasonic sensor according to claim 1, wherein said flexible hollow shafts are formed of helically wound spring wire having mutually interlocking windings.

* * * * *